United States Patent
D'Antonio

[11] Patent Number: 5,810,831
[45] Date of Patent: Sep. 22, 1998

[54] FEMORAL SIZING GUIDE AND METHOD

[75] Inventor: James A. D'Antonio, Sewickley, Pa.

[73] Assignee: Osteonics Corp., Allendale, N.J.

[21] Appl. No.: 963,127

[22] Filed: Oct. 28, 1997

Related U.S. Application Data

[63] Continuation of Ser. No. 197,170, Feb. 16, 1994, abandoned.

[51] Int. Cl.$^6$ .................................................. A61B 17/56
[52] U.S. Cl. ............................................ 606/88; 606/102
[58] Field of Search ................................ 606/88, 87, 89,
606/96, 102, 86, 79, 80, 82; 623/20, 18;
33/512, 511

[56] References Cited

U.S. PATENT DOCUMENTS

| | | | |
|---|---|---|---|
| 4,567,886 | 2/1986 | Petersen | 606/88 X |
| 4,599,086 | 7/1986 | Doty | 623/17 |
| 4,703,751 | 11/1987 | Pohl | 606/62 |
| 4,722,330 | 2/1988 | Russell et al. | 606/88 X |
| 4,759,350 | 7/1988 | Dunn et al. | |
| 4,892,093 | 1/1990 | Zarnowski et al. | 606/82 |
| 5,035,700 | 7/1991 | Kenna | 606/88 |
| 5,282,803 | 2/1994 | Lackey | 606/80 |
| 5,454,816 | 10/1995 | Ashby | 606/88 |

FOREIGN PATENT DOCUMENTS

| | | | |
|---|---|---|---|
| 340176 | 11/1989 | European Pat. Off. | 606/89 |
| 380451 | 8/1990 | European Pat. Off. | |
| 538153 | 4/1993 | European Pat. Off. | 606/88 |
| 2664157 | 1/1992 | France | |
| 2679766 | 2/1993 | France | 606/88 |

OTHER PUBLICATIONS

MGII Total Knee System Surgical Technique, Zimmer (undated) date unknown, author unknown, pp. 1–40.

*Primary Examiner*—Guy V. Tucker
*Attorney, Agent, or Firm*—Arthur Jacob

[57] ABSTRACT

A femoral sizing guide of the type in which a sizing guide block is located at the distal femur utilizing locator feet for engaging the posterior condyles to assist in the location of a femoral cutting guide of suitable size in the implant of a femoral knee prosthesis includes a coupling arrangement by which locator feet of selected size are independently coupled interoperatively with the sizing guide block for enabling a surgeon to compensate for conditions encountered at the implant site, during the implant procedure, and attain a stable placement of the femoral sizing guide at the distal femur for accurate sizing and location of the femoral knee prosthesis.

21 Claims, 3 Drawing Sheets

FEMORAL SIZING GUIDE AND METHOD

This application is a continuation, of application Ser. No. 08/197,170 filed Feb. 16, 1994, now abandoned.

BACKGROUND OF THE INVENTION

1. Field of the Invention

The present invention relates generally to the implant of prosthetic joints and pertains, more specifically, to the preparation of the distal femur for the implant of a femoral knee prosthesis, utilizing a femoral sizing guide for the subsequent location of a femoral cutting guide to assist in establishing the surfaces necessary for locating and securing the prosthesis in place on the femur.

The implant of a prosthetic knee joint requires that the distal femur be prepared to receive the femoral component of the knee prosthesis by cutting the bone of the femur to establish accurately located surfaces against which the femoral knee prosthesis will rest upon implant of the femoral component. Various guides are available to the surgeon for assisting in guiding a saw blade during use of the saw blade to make the cuts which establish the desired surfaces. These guides usually are located and secured upon a transverse surface established initially on the distal femur to provide guide surfaces for guiding the saw blade during the execution of an axially directed anterior femoral cut, an axially directed posterior femoral cut, an anterior chamfer and a posterior chamfer, all specifically related to the size of the femoral knee prosthesis to be implanted. The appropriate location of a femoral cutting guide, then, generally requires the use of a femoral sizing guide to determine the size of the femoral knee prosthesis which will be implanted in a particular recipient, and to locate the corresponding femoral cutting guide appropriately on the transverse distal femoral surface.

2. Description of The Related Art

A preferred femoral sizing guide currently in use employs the posterior condyles of the distal femur for reference surfaces with which the femoral sizing guide is engaged during the sizing procedure. Thus, the femoral sizing guide includes a sizing guide block, for placement against the transverse distal femoral surface, and locator feet projecting axially from the sizing guide block to engage the posterior condyles. However, it has been observed that the fixed relationship between the locator feet and the sizing guide block can restrict the ability to compensate for various conditions encountered at the implant site, with the result that the selection of a particular femoral sizing guide can lead to some compromises in the location of the implanted femoral knee prosthesis. During the actual implant procedure, the surgeon may determine that it would be advantageous to remove more or less bone from a particular posterior condyle than that which is dictated by the fixed locator feet of a selected femoral sizing guide in order to compensate for a particular condition observed interoperatively. For example, conditions at the implant site may require the removal of slightly more bone at the distal end of the femur than would ordinarily be removed for the particular size of the femoral knee prosthesis which is to be implanted at the site. In such an instance, it would be desirable to locate the femoral cutting guide for the removal of sightly more bone from one or both of the posterior condyles, so as to equalize the flexion/extension gap. Further, absent cartilage on a worn posterior condyle, or erosion or atrophy, as is frequently observed in valgus knees with an atrophic posterior femoral condyle, are conditions which could force an internal rotation positioning of a femoral sizing guide having fixed locator feet, with concomitant internal rotation positioning of the femoral cutting guide, leading to an undesirable preparation. These conditions often cause unstable seating of the femoral sizing guide and require the surgeon to approximate, by eye, the best position for the femoral sizing guide. In addition, where the femoral sizing guide indicates a size which falls between available standard sizes, the surgeon must make the best guess at which size to select and then must rely upon an approximated location of the femoral cutting guide for the selected size.

SUMMARY OF THE INVENTION

The present invention enables the surgeon, interoperatively, to compensate for conditions encountered at the implant site when utilizing a femoral sizing guide to determine the size of the femoral knee prosthesis to be implanted, and the accurate location of a femoral cutting guide of appropriate size. As such, the present invention attains several objects and advantages, some of which are summarized as follows: Enables the surgeon to select, interoperatively, during the sizing procedure, a predetermined amount of bone to be removed from the posterior condyles for subsequent accurate positioning of a femoral cutting guide, with compensation for conditions encountered at the implant site; allows an opportunity to compensate, interoperatively, for absent cartilage on a worn posterior condyle, or for bone erosion or atrophy, during the sizing procedure; enables a stable preparation for the appropriate size femoral knee prosthesis when the sizing procedure initially indicates a size which falls in-between standard available sizes; provides increased stability in the location of a femoral sizing guide at the distal femur; lessens the risk of creating an undesirable preparation at the distal femur; provides the surgeon with an advantageous technique for increasing the accuracy of the sizing procedure and concomitant accurate location of an appropriate femoral cutting guide, with added ease and lessened time; minimizes the need for guessing or for visual estimation in determining proper sizing and proper positioning of a femoral cutting guide, and especially proper rotational positioning, during femoral preparations for the implant of a femoral knee prosthesis; permits the surgeon to create a predictable posterior femoral condylar resection for exemplary performance in the completed implanted knee prosthesis.

The above objects and advantages, as well as further objects and advantages, are attained by the present invention which may be described briefly as a femoral sizing guide for use in determining, interoperatively, the size of a femoral knee prosthesis to be implanted at the prepared distal femur of a femur extending in an axial direction within a recipient, the femoral sizing guide being arranged for location against the distal femoral surface and the posterior condylar surfaces of the distal femur and enabling interoperative compensation for variations in the conditions encountered at the posterior condylar surfaces when determining the amount of bone to be removed from the posterior condyles, the femoral sizing guide comprising: a femoral sizing guide block having a block locator surface for extending transverse to the axial direction to engage the distal surface of the distal femur, and guide means for determining the location of a femoral cutting guide to be placed subsequently at the distal femur; foot means for projecting in the axial direction, the foot means including foot locator surfaces for engaging the posterior condylar surfaces when the block locator surface is engaged with the distal femoral surface to determine the amount of bone to be removed from the posterior condyles; coupling means for selectively coupling the foot means with the femoral sizing guide block, and selectively uncoupling the foot means from the femoral sizing guide block, interoperatively, to enable the selection of foot means of predetermined size from a plurality of available foot means of different sizes for coupling with the femoral sizing guide block, the selected foot means of predetermined size placing the foot locator surfaces in position to accommodate the conditions encountered at the posterior condylar surfaces and enable direct determination of the amount of bone to be removed.

The invention further includes a method for determining, interoperatively, the size of a femoral knee prosthesis to be implanted at the prepared distal femur of a femur extending in an axial direction within a recipient, the method including locating a femoral sizing guide against the distal femoral surface and the posterior condylar surfaces of the distal femur and enabling interoperative compensation for variations in the conditions encountered at the posterior condylar surfaces when determining the amount of bone to be removed from the posterior condyles, the femoral sizing guide including a femoral sizing guide block having a block locator surface for extending transverse to the axial direction to engage the distal surface of the distal femur, guide means for determining the location of a femoral cutting guide to be placed subsequently at the distal femur, and foot means for projecting in the axial direction, the foot means including foot locator surfaces for engaging the posterior condylar surfaces when the block locator surface is engaged with the distal femoral surface to determine the amount of bone to be removed from the posterior condyles, the method comprising: selecting foot means of predetermined size from a plurality of foot means of different sizes; coupling the selected foot means with the femoral sizing guide block, interoperatively, to place the corresponding foot locator surfaces in position to accommodate the conditions encountered at the posterior condylar surfaces and enable direct determination of the amount of bone to be removed.

BRIEF DESCRIPTION OF THE DRAWING

The invention will be understood more fully, while still further objects and advantages will become apparent, in the following detailed description of preferred embodiments of the invention illustrated in the accompanying drawing, in which.

DESCRIPTION OF THE PREFERRED EMBODIMENTS

Figure 1:
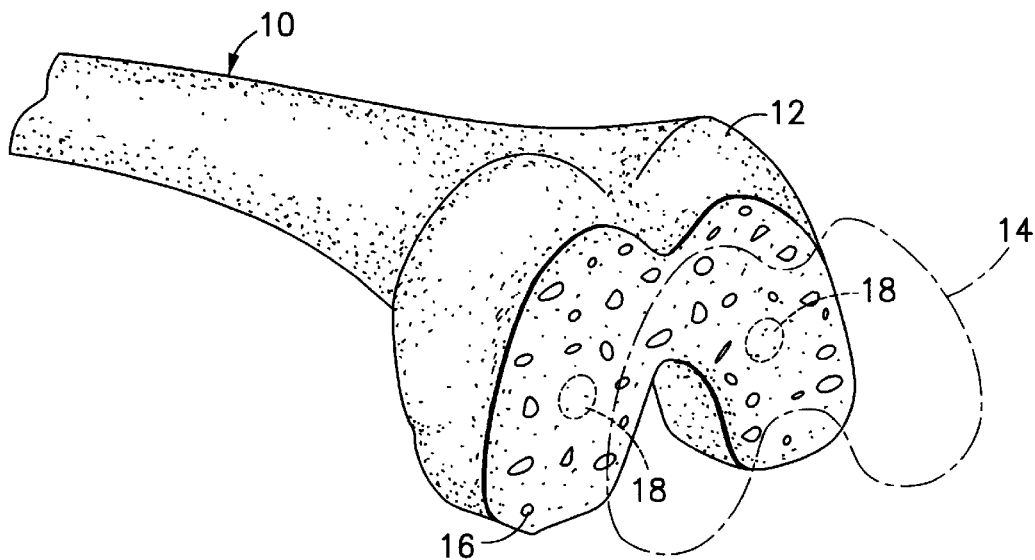
FIG. 1 is a pictorial perspective view of a distal femur, prepared with a transverse distal femoral surface.

Referring now to the drawing, and especially to FIG. 1 thereof, a femur is illustrated at 10 and is seen to have a distal end 12 which has undergone initial preparation for the implant of a femoral component of a knee prosthesis (not shown) to the extent that a distal portion (shown in phantom at 14) has been removed and a transverse distal surface 16 extending transverse to the axial direction of the femur 10, has been established at the distal end 12. Transverse distal surface 16 is planar, and a pair of axially extending holes 18 are to be drilled into the bone of the femur 10 for the reception and location of a femoral cutting guide (not shown) which will be used to complete the preparation of the distal femur, as explained in detail in U.S. Pat. No. 4,892,093.

Figure 2:
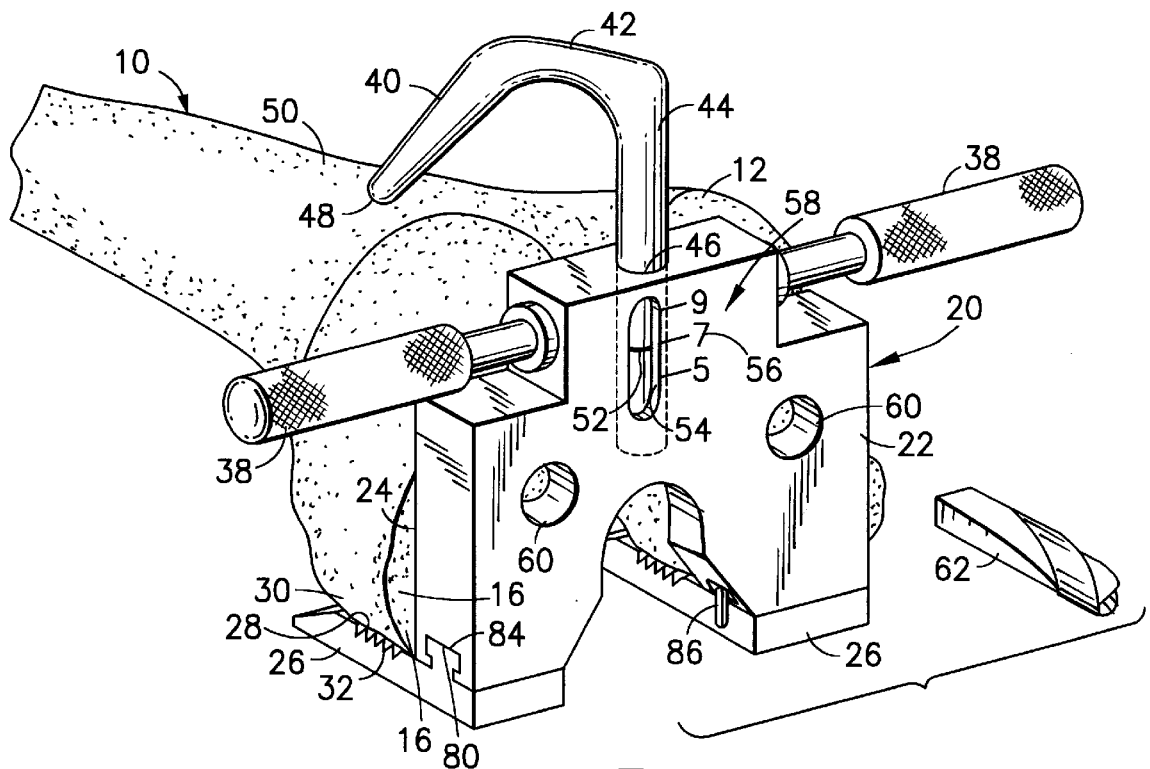
FIG. 2 is a pictorial perspective view, enlarged over FIG. 1, showing a femoral sizing guide constructed in accordance with the present invention, placed at the distal femur.
Figure 3:
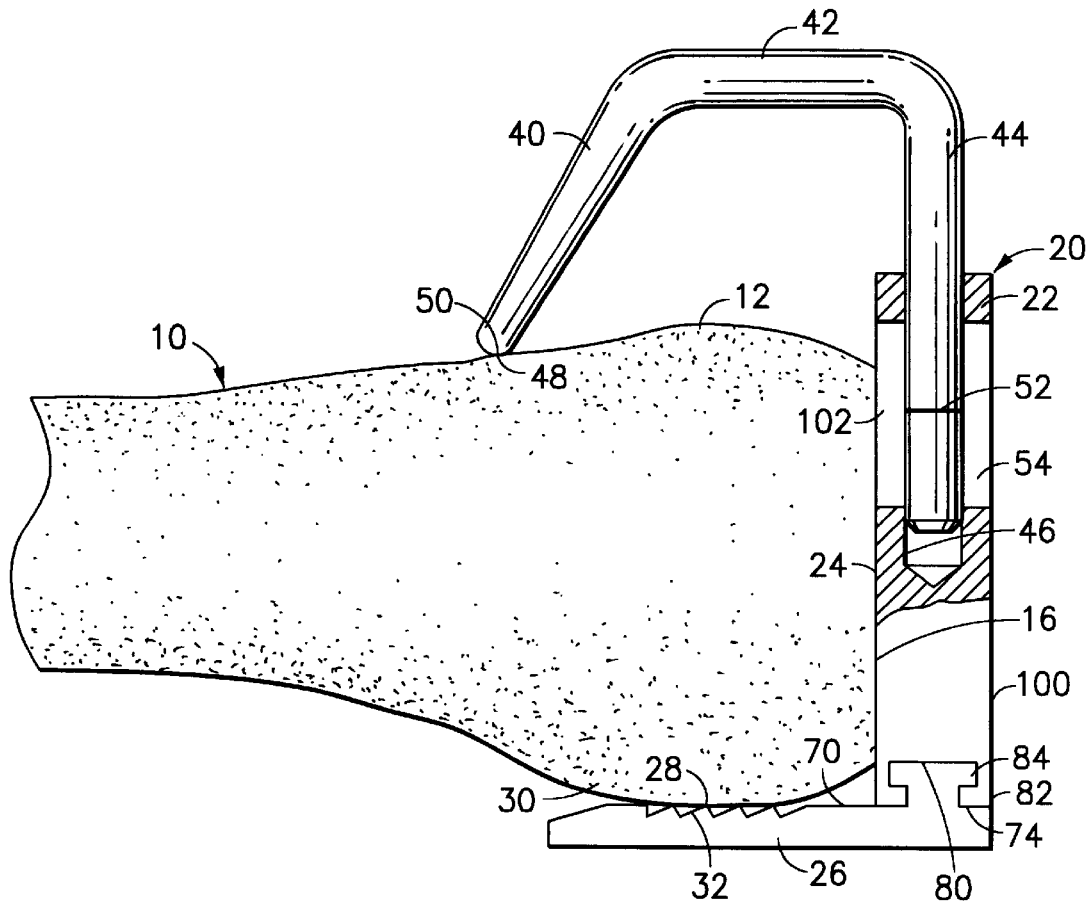
FIG. 3 is a longitudinal elevational view, partially in cross-section, of the femoral sizing guide on the distal femur.
Figure 4:
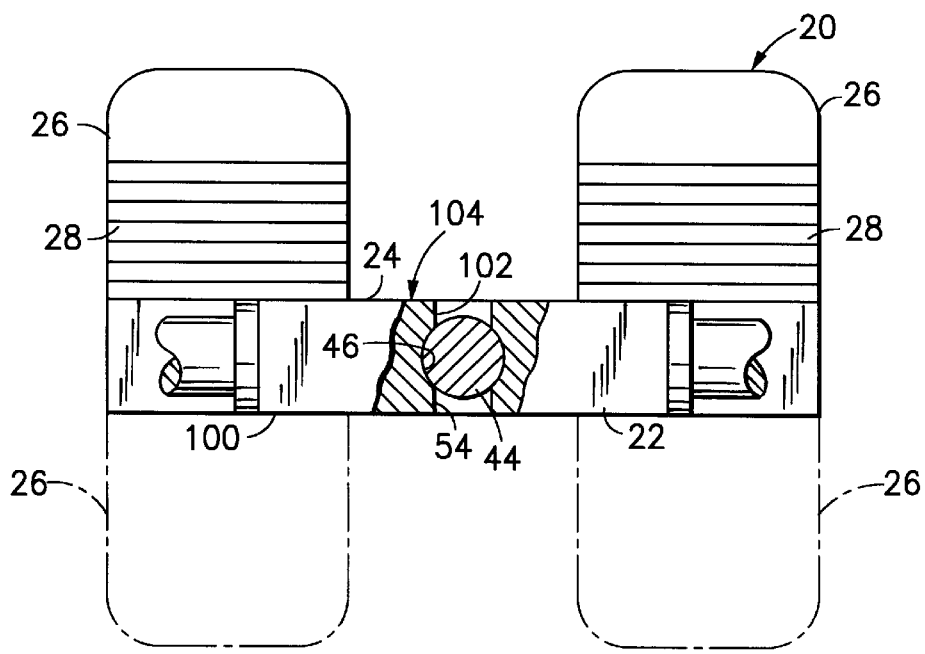
FIG. 4 is a top plan view, partially in cross-section, of the femoral sizing guide.

Turning now to FIGS. 2 through 4, in order to determine the size of the femoral knee prosthesis and place the holes 18 for the reception of a femoral cutting guide of corresponding size in appropriate location and orientation relative to the distal femur, a femoral sizing guide constructed in accordance with the invention is illustrated at 20 and is placed against the distal end 12 of femur 10. Femoral sizing guide 20 includes a femoral sizing guide block 22 having a planar locator surface 24 which is seated upon the transverse distal surface 16 and extending in lateral and altitudinal directions relative to the axial directions of the femur 10. Foot means in the form of a pair of laterally spaced apart locator feet 26 are integrated with the sizing guide block 22 and project in longitudinal directions, relative to the lateral and altitudinal directions of the planar locator surface 24, essentially normal to the planar locator surface 24, and to the transverse distal surface 16. Each foot 26 includes a foot locator surface 28 which, in the illustrated embodiment, is serrated. Upon proper seating of the femoral sizing guide 20 at the distal end 12 of the femur 10, planar locator surface 24 is placed against transverse distal surface 16 and the feet 26 are placed against the condyles 30 of the distal femur, with the foot locator surfaces 28 engaging respective posterior condylar surfaces 32. Handles 38 assist in maintaining the femoral sizing guide 20 in place upon the distal femur.

The size of the femoral knee prosthesis to be implanted is determined by the use of a stylus 40 which depends from a stylus arm 42 extending from a cylindrical post 44 received within a complementary socket 46 in the sizing guide block 22. Stylus 40 includes a stylus tip 48 which is traced manually across the anterior cortex 50 of the distal femur, in a medial/lateral direction, while the sizing guide block 22 is held in place upon the distal femur, in the position described above. As the stylus tip 48 follows the contour of the anterior cortex 50, an index mark 52 on the post 44 is viewed through a window 54 in the sizing guide block 22 and generally will be registered with a size designation 56 on a scale 58 placed adjacent the window 54. Observation of the index mark 52 enables the surgeon to determine the appropriate size of the femoral knee prosthesis to be implanted. Once the size is determined, holes 18 are drilled in the distal femur, employing a pair of fixed drill guide openings 60 provided in the sizing guide block 22 to guide a drill 62, thereby assuring the appropriate subsequent location of the femoral cutting guide on the distal femur.

It will be appreciated that the accuracy with which the holes 18 are located determines the accuracy of the placement of the femoral cutting guide at the distal femur and, consequently, the accuracy of the location of the femoral knee prosthesis being implanted. Since femoral sizing guide 20 is of the type described above, in which the posterior condylar surfaces 32 are employed as reference surfaces, the presence of certain conditions at the posterior condylar surfaces 32, such as those outlined above, can affect the seating of the femoral sizing guide 20 on the distal femur and the accuracy with which holes 18 are located. These conditions may not necessarily be detected until actually observed by the surgeon during the implant dure. Hence, femoral sizing guide 20 is constructed so as to enable the surgeon to compensate for any such conditions interoperatively.

Figure 5:
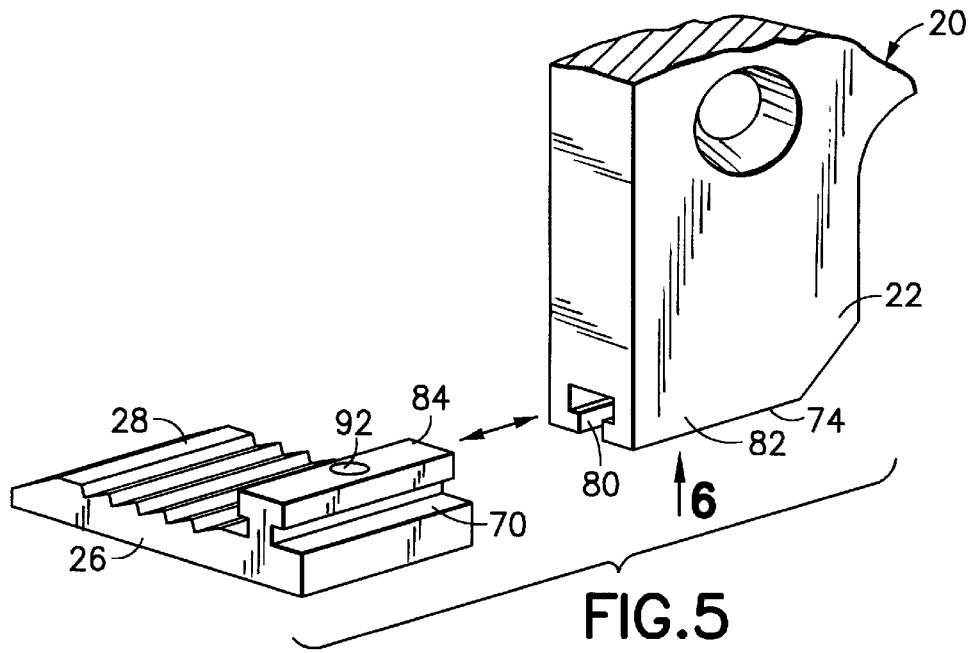
FIG. 5 is an enlarged fragmentary exploded perspective view of a portion of the femoral sizing guide and illustrating the method of the invention.
Figure 6:
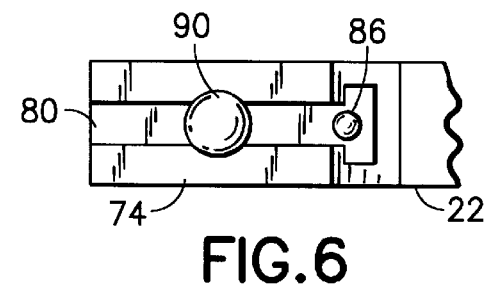
FIG. 6 is a fragmentary bottom plan view of a portion of the femoral sizing guide viewed in the direction of the arrow in FIG. 5.
Figure 7:
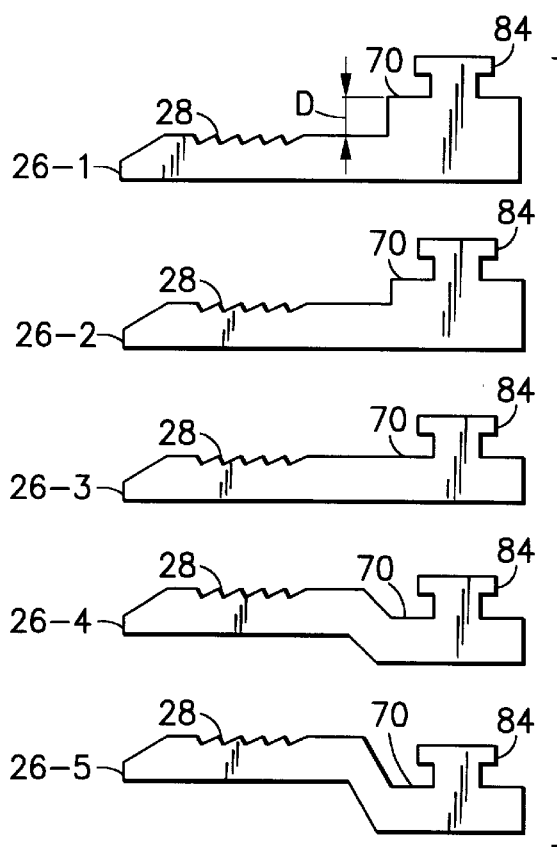
FIG. 7 is a side elevational view showing several alternative component parts of the femoral sizing guide for carrying out the method of the invention.

Accordingly, turning now to FIGS. 5 and 6, each locator foot 26 is coupled with the sizing guide block 22 by coupling means which permit selective uncoupling of the locator foot 26 for removal and replacement with a corresponding locator foot selected from a plurality of available locator feet, as illustrated by locator feet 26-1, 26-2, 26-3, 26-4 and 26-5 in FIG. 7. Each locator foot 26-1, 26-2, 26-3, 26-4 and 26-5 is of a different size; that is, the locator surface 28 provided by each locator foot 26-1, 26-2, 26-3, 26-4 and 26-5 is spaced from a datum surface 70, in the anterior/posterior direction, which direction is altitudinal with respect to the longitudinal direction of the locator foot, by a different amount, represented by the distance D. The datum surface 70 of an inserted locator foot 26 is coincident with the basal surface 74 of the sizing guide block 22. Hence, the choice of a particular locator foot 26 as a medial locator foot for engagement with the medial posterior condyle, and the choice of a particular locator foot 26 as a lateral locator foot for engagement with the lateral posterior condyle, will space the openings 60 in the sizing guide block 22, in the anterior/posterior direction, by a corresponding selected amount so that the surgeon may choose a particular locator foot 26 to select a predetermined amount of bone to be removed from each posterior portion of condyles 30. In this manner, the surgeon can assure that the appropriate amount of bone is removed to equalize, or balance, the flexion/extension gap, or to compensate for other conditions encountered at the posterior condylar surface 32 against which the selected locator foot will be placed so as to attain a stable positioning of the femoral sizing guide 20 for accurate location of the holes 18.

The illustrated preferred coupling means includes complementary interengaging sliding elements on the sizing guide block 22 and on each locator foot 26, the sliding elements including a groove 80 extending in the lateral, or medial/lateral direction along the basal portion 82 of the sizing guide block 22, and a spline 84 extending along each locator foot 26, in the lateral, or medial/lateral direction. Each spline 84 has an ultitudinal, or anterior/posterior cross-sectional configuration complementary to the ultitudinal, or anterior/posterior cross-sectional configuration of the corresponding groove 80 so that upon coupling a selected locator foot 26 with the sizing guide block 22, the spline 84 of the selected locator foot 26 is received within the groove 80 in the sizing guide block 22 for sliding movement into a fully-engaged position, where the locator foot 26 is coupled appropriately with the sizing guide block 22. Thus, the complementary interlocking spline 84 and groove 80 preclude relative movement between the sizing guide block 22 and each locator foot 26 in altitudinal, or anterior/posterior directions, while enabling deliberate relative sliding movement in medial/lateral directions for coupling and uncoupling the sizing guide block 22 and each locator foot 26. The preferred cross-sectional configuration for the spline 84 and for the counterpart groove 80 is a T-shaped cross-sectional configuration, as illustrated, the T-shaped cross-sectional configuration providing the necessary stability in the coupling, together with ease of operation during the implant procedure.

A stop pin 86 engages the locator foot 26 when the locator foot 26 is at the fully-engaged position to assure positive location of the locator foot 26 at the fully-engaged position. A detent arrangement includes a resiliently biased spherical detent element 90 in the sizing guide block 22 in position to engage a complementary spherical depression 92 in the spline 84 of the locator foot 26 to secure the locator foot 26 at the fully-engaged position. Selective uncoupling of the locator foot 26 is attained by reverse sliding movement of the spline 84 so as to move the spline 84 out of the groove 80, against the bias of the detent arrangement, to disengage the spline 84 from the groove 80, and the locator foot 26 from the sizing guide block 22, thereby placing the locator foot 26 in a fully-disengaged position, as seen in FIG. 5.

As best seen in FIG. 7, the different size locator feet 26-1, 26-2, 26-3, 26-4, and 26-5 differ by virtue of the location of the locator surface 28 relative to the datum surface 70 on the locator foot 26, which datum surface 70 engages the basal surface 74 of the sizing guide block 22 when the locator foot 26 is coupled with the sizing guide block 22. The differences are incremental differences marked for ease of identification so that the selection of the appropriate locator foot 26 is simplified. Since each selected lateral locator foot 26 is coupled with the sizing guide block 22 independent of the selected medial locator foot 26 in a fully-assembled femoral sizing guide 20, the surgeon can select the amount of bone to be removed from each of the posterior lateral condyle and the posterior medial condyle, independently, thereby assuring stable seating of the femoral sizing guide 20 on the distal femur under any one of a variety of conditions encountered at the implant site. Thus, proper rotation can be attained by the independent determination of the amount of bone to be removed from each of the posterior lateral condyle and the posterior medial condyle. In addition, during the above-described sizing procedure, should the stylus 40 indicate a size between two standard available sizes of the femoral knee prosthesis to be implanted, locator feet 26 can be selected to displace the sizing guide block 22 slightly in the anterior direction, thereby placing the sizing guide block 22 in appropriate position to accommodate a single selected size for the femoral knee prosthesis. In the illustrated embodiment, the drill guide openings 60 are located for a predetermined rotational orientation of the holes 18. Since the rotational orientation for a left knee is a mirror image of the rotational orientation for a right knee, sizing guide block 22 is provided with a further planar locator surface 100 placed axially opposite the planar locator surface 24 so that the same sizing guide block 22 is available for use in connection with the implant of a left knee prosthesis or a right knee prosthesis. Thus, by uncoupling and releasing the locator feet 26 from the sizing guide block 22 and then coupling the locator feet 26 so that the locator feet 26 project from the further planar locator surface 100, as illustrated in phantom in FIG. 4, the femoral sizing guide 20 is reversed for universal use. It is noted that the detent arrangement, which includes detent element 90 and depression 92, is so located as to permit securement of the locator feet 26 at the fully-engaged position in the reversed configuration of sizing guide block 22. a further window 102 is located diametrically opposite window 54, and a further scale is placed at 104, adjacent the further window 102, duplicating the corresponding arrangement of window 54 and scale 58, for determining the size of the femoral knee prosthesis, as described above.

It will be seen that the present invention attains the several objects and advantages summarized above, namely: Enables the surgeon to select, interoperatively, during the sizing procedure, a predetermined amount of bone to be removed from the posterior condyles for subsequent accurate positioning of a femoral cutting guide, with compensation for conditions encountered at the implant site; allows an opportunity to compensate, interoperatively, for absent cartilage on a worn posterior condyle, or for bone erosion or atrophy, during the sizing procedure; enables a stable preparation for the appropriate size femoral knee prosthesis when the sizing procedure initially indicates a size which falls in-between standard available sizes; provides increased stability in the location of a femoral sizing guide at the distal femur; lessens the risk of creating an undesirable preparation at the distal femur; provides the surgeon with an advantageous technique for increasing the accuracy of the sizing procedure and concomitant accurate location of an appropriate femoral cutting guide, with added ease and lessened time; minimizes the need for guessing or for visual estimation in determining proper sizing and proper positioning of a femoral cutting guide, and especially proper rotational positioning, during femoral preparations for the implant of a femoral knee prosthesis; permits the surgeon to create a predictable posterior femoral condylar resection for exemplary performance in the completed implanted knee prosthesis.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An improvement for facilitating the use of a femoral sizing guide in determining, interoperatively, the size of a femoral knee prosthesis to be implanted at a prepared distal femur of a femur extending in an axial direction within a recipient, the femoral sizing guide being arranged for location against the distal femoral surface and the posterior condylar surfaces of the prepared distal femur, the improvement enabling interoperative compensation for variations in the conditions encountered at the posterior condylar surfaces when determining the amount of bone to be removed from the posterior condyles, the posterior condylar surfaces including a medial condylar surface and a lateral condylar surface, the improvement comprising:

a femoral sizing guide block having a block locator surface extending in lateral and altitudinal directions for extending transverse to the axial direction when engaged with the prepared distal surface of the distal femur, and guide means for determining the location of a femoral cutting guide to be placed subsequently at the distal femur;

foot means for projecting in a longitudinal direction relative to the lateral and altitudinal directions of the block locator surface, the foot means including foot locator surfaces for engaging the posterior condylar surfaces when the block locator surface is engaged with the distal femoral surface, the foot means further including a medial foot having a medial locator surface for engaging the medial condylar surface, and a lateral foot having a lateral locator surface for engaging the lateral condylar surface; and coupling means including an independent coupling arrangement for at least one of the medial foot and the lateral foot, such that said at least one of the medial foot and the lateral foot is selectively coupled with and is selectively uncoupled from the femoral sizing guide block, interoperatively, independent of the other of the medial foot and the lateral foot to enable the selection of said one of the medial foot and the lateral foot of predetermined size from a plurality of available foot means of different sizes for coupling with the femoral sizing guide block, the selected one of the medial foot and the lateral foot of predetermined size placing the corresponding one of the medial locator surface and the lateral locator surface in position relative to the other of the medial locator surface and the lateral locator surface to accommodate the conditions encountered at the posterior condylar surfaces and enable direct determination of the amount of bone to be removed.

2. The invention of claim 1 wherein:

the coupling means include an independent coupling arrangement for each of the medial foot and the lateral foot, such that either one of the medial foot and the lateral foot is selectively coupled with and uncoupled from the sizing guide block.

3. The invention of claim 2 wherein each coupling arrangement includes interengaging complementary sliding elements on the sizing guide and on each of the medial foot and the lateral foot, the sliding elements being selectively engaged and disengaged by relative sliding movement between the sizing guide block and the corresponding foot in a lateral direction between a fully-engaged position, wherein the corresponding foot is coupled with the sizing guide block, and a fully-disengaged position, wherein the corresponding foot is uncoupled from the sizing guide block.

4. The invention of claim 3 including securing means for securing each foot against movement relative to the sizing guide block when the foot is at the fully-engaged position.

5. The invention of claim 4 wherein the securing means includes a detent for releasibly securing each foot at the corresponding fully-engaged position.

6. The invention of claim 3 wherein the interengaging sliding elements include a groove extending in the lateral direction and having an altitudinal cross-sectional configuration, and a spline extending in the lateral direction and having an altitudinal cross-sectional configuration complementary to the corresponding cross-sectional configuration of the groove, the complementary cross-sectional configurations interlocking to preclude relative movement between the sizing guide block and each foot in altitudinal directions while enabling relative sliding movement in lateral directions for coupling and uncoupling the sizing guide block and each foot.

7. The invention of claim 6 wherein the complementary cross-sectional configurations are T-shaped.

8. The invention of claim 1 wherein:

the sizing guide block includes a further locator surface placed longitudinally opposite the block locator surface for enabling reversal of the sizing guide block to engage the further locator surface with the distal femoral surface; and the coupling means includes a coupling configuration for enabling the foot means to be coupled with the sizing guide block so as to engage the posterior condylar surfaces when the further locator surface is engaged with the distal femoral surface.

9. The invention of claim 8 wherein:

the coupling means include an independent coupling arrangement for each of the medial foot and the lateral foot, such that either one of the medial foot and the lateral foot is selectively coupled with and uncoupled from the sizing guide block.

10. The invention of claim 9 wherein each coupling arrangement includes interengaging complementary sliding elements on the sizing guide and on each of the medial foot and the lateral foot, the sliding elements being selectively engaged and disengaged by relative sliding movement between the sizing guide block and the corresponding foot in a lateral direction between a fully-engaged position, wherein the corresponding foot is coupled with the sizing guide block, and a fully-disengaged position, wherein the corresponding foot is uncoupled from the sizing guide block.

11. The invention of claim 10 including securing means for securing each foot against movement relative to the sizing guide block when the foot is at the fully-engaged position.

12. The invention of claim 11 wherein the securing means includes a detent for releasibly securing each foot at the corresponding fully-engaged position.

13. The invention of claim 12 wherein the interengaging sliding elements include a groove extending in the lateral direction and having an altitudinal cross-sectional configuration, and a spline extending in the lateral direction and having an altitudinal cross-sectional configuration complementary to the corresponding cross-sectional configuration of the groove, the complementary cross-sectional configurations interlocking to preclude relative movement between the sizing guide block and each foot in altitudinal directions while enabling relative sliding movement in lateral directions for coupling and uncoupling the sizing guide block and each foot.

14. The invention of claim 1 wherein the distal femur includes an anterior cortex and the sizing guide includes:
 a sizing stylus for mounting upon the sizing guide block for movement in anterior/posterior directions to enable engagement of the stylus with the anterior cortex of the distal femur when the block locator surface is engaged with the distal femoral surface; and
 indicator means coupled with the stylus for providing an indication of the size of the femoral knee prosthesis to be implanted, based upon the anterior/posterior position of the stylus relative to the sizing guide block when the stylus is engaged with the anterior cortex.

15. The invention of claim 14 wherein:
 the coupling means include an independent coupling arrangement for each of the medial foot and the lateral foot, such that either one of the medial foot and the lateral foot is selectively coupled with and uncoupled from the sizing guide block.

16. The invention of claim 15 wherein each coupling arrangement includes interengaging complementary sliding elements on the sizing guide and on each of the medial foot and the lateral foot, the sliding elements being selectively engaged and disengaged by relative sliding movement between the sizing guide block and the corresponding foot in a lateral direction between a fully-engaged position, wherein the corresponding foot is coupled with the sizing guide block, and a fully-disengaged position, wherein the corresponding foot is uncoupled from the sizing guide block.

17. The invention of claim 16 including securing means for securing each foot against movement relative to the sizing guide block when the foot is at the fully-engaged position.

18. The invention of claim 17 wherein the securing means includes a detent for releasibly securing each foot at the corresponding fully-engaged position.

19. The invention of claim 18 wherein the interengaging sliding elements include a groove extending in the lateral direction and having an altitudinal cross-sectional configuration, and a spline extending in the lateral direction and having an altitudinal cross-sectional configuration complementary to the corresponding cross-sectional configuration of the groove, the complementary cross-sectional configurations interlocking to preclude relative movement between the sizing guide block and each foot in altitudinal directions while enabling relative sliding movement in lateral directions for coupling and uncoupling the sizing guide block and each foot.

20. An improvement for facilitating the determination, interoperatively, of the size of a femoral knee prosthesis to be implanted at a prepared distal femur of a femur extending in an axial direction within a recipient, the determination including locating a femoral sizing guide against the distal femoral surface and the posterior condylar surfaces of the prepared distal femur, the improvement enabling interoperative compensation for variations in the conditions encountered at the posterior condylar surfaces when determining the amount of bone to be removed from the posterior condyles, the posterior condylar surfaces including a medial condylar surface and a lateral condylar surface, the femoral sizing guide including a femoral sizing guide block having a block locator surface extending in lateral and altitudinal directions for extending transverse to the axial direction when engaged with the prepared distal surface of the distal femur, guide means for determining the location of a femoral cutting guide to be placed subsequently at the distal femur, and foot means for projecting in a longitudinal direction relative to the lateral and altitudinal directions of the block locator surface, the foot means including foot locator surfaces for engaging the posterior condylar surfaces when the block locator surface is engaged with the distal femoral surface to determine the amount of bone to be removed from the posterior condyles, the foot means further including a medial foot having a medial locator surface for engaging the medial condylar surface, and a lateral foot having a lateral locator surface for engaging the lateral condylar surface, the improvement comprising the steps of:
 selecting at least one of the medial foot and the lateral foot of predetermined size from a plurality of foot means of different sizes; and
 coupling the selected one of the medial foot and the lateral foot with the femoral sizing guide block, independent of the other of the medial foot and the lateral foot, interoperatively, such that the selected one of the medial foot and the lateral foot is coupled to the femoral sizing guide block to place the corresponding one of the medial locator surface and lateral locator surface relative to the other of the medial locator surface and the lateral locator surface for location of the foot locator surfaces in position to accommodate the conditions encountered at the posterior condylar surfaces and enable direct determination of the amount of bone to be removed.

21. The invention of claim 20 wherein
 the step of coupling the selected foot means with the femoral sizing guide block includes independently coupling each of the medial foot and the lateral foot with the femoral sizing guide block, such that either one of the medial foot and the lateral foot is selectively coupled with the femoral sizing guide block.

* * * * *